United States Patent
Wennberg

(10) Patent No.: US 8,095,380 B2
(45) Date of Patent: Jan. 10, 2012

(54) SYSTEMS AND METHODS FOR PREDICTING HEALTHCARE RELATED FINANCIAL RISK

(75) Inventor: David E. Wennberg, Cape Elizabeth, ME (US)

(73) Assignee: Health Dialog Services Corporation, Boston, MA (US)

( * ) Notice: Subject to any disclaimer, the term of this patent is extended or adjusted under 35 U.S.C. 154(b) by 1022 days.

(21) Appl. No.: 11/281,233

(22) Filed: Nov. 16, 2005

(65) Prior Publication Data

US 2006/0129428 A1 Jun. 15, 2006

Related U.S. Application Data

(60) Provisional application No. 60/628,476, filed on Nov. 16, 2004, provisional application No. 60/628,504, filed on Nov. 16, 2004, provisional application No. 60/628,212, filed on Nov. 16, 2004.

(51) Int. Cl.
*G06Q 50/00* (2006.01)
(52) U.S. Cl. .......................................................... 705/2
(58) Field of Classification Search ....................... 705/2
See application file for complete search history.

(56) References Cited

U.S. PATENT DOCUMENTS

| | | | |
|---|---|---|---|
| 5,778,345 A * | 7/1998 | McCartney | 705/2 |
| 6,061,657 A * | 5/2000 | Whiting-O'Keefe | 705/2 |
| 6,223,164 B1 | 4/2001 | Seare et al. | |
| 6,266,645 B1 * | 7/2001 | Simpson | 705/3 |
| 6,484,144 B2 | 11/2002 | Martin et al. | |
| 6,611,846 B1 | 8/2003 | Stoodley | |
| 6,802,810 B2 | 10/2004 | Ciarniello et al. | |
| 7,222,079 B1 * | 5/2007 | Seare et al. | 705/3 |
| 2001/0016821 A1 | 8/2001 | DeBusk et al. | |
| 2002/0087358 A1 | 7/2002 | Gilbert | |
| 2002/0099686 A1 * | 7/2002 | Schwartz et al. | 707/1 |
| 2003/0050794 A1 | 3/2003 | Keck | |
| 2003/0195772 A1 * | 10/2003 | Meek et al. | 705/2 |
| 2004/0039600 A1 * | 2/2004 | Kramer et al. | 705/2 |
| 2004/0039710 A1 | 2/2004 | McMillan et al. | |
| 2006/0173663 A1 | 8/2006 | Langheier et al. | |

OTHER PUBLICATIONS

International Search Report and Written Opinion mailed Jun. 17, 2008.
Non-Final Office Action dated Oct. 19, 2009 and Response dated Feb. 16, 2010 in U.S. Appl. No. 11/280,611.
Final Office Action dated May 11, 2010 in U.S. Appl. No. 11/280,611.
Non-Final Office Action dated Dec. 7, 2009 and Response dated Jun. 4, 20120 in U.S. Appl. No. 11/542,574.
Final Office Action dated Aug. 12, 2010 in U.S. Appl. No. 11/542,574.

* cited by examiner

*Primary Examiner* — Gerald J. O'Connor
*Assistant Examiner* — Hiep V Nguyen
(74) *Attorney, Agent, or Firm* — Ropes & Gray LLP

(57) ABSTRACT

A system for predicting healthcare financial risk including the process of accessing patient data associated with one or more patents, accessing geographic and healthcare system data, filtering the patient data, geographic data, and healthcare system data into clean data, and applying a predictive risk model to the clean data to generate patient profile data and to identify a portion of the patients associated with a level of predicted financial risk.

30 Claims, 11 Drawing Sheets

- Abdominal Aortic Aneurysm Repair per 1000 Enrollees
- Admissions for Acute Myocardial Infarction per 1000 Enrollees
- All Medical Discharges per 1000 Enrollees
- All Physicians per 100000 Residents
- All Surgical Discharges per 1000 Enrollees
- Allergists/Immunologists per 100000 Residents
- Allocated Cardiac Catheterization Laboratories per 100000 Residents
- Anesthesiologists per 100000 Residents
- Aortic Valve Replacement per 1000 Enrollees
- Aortic/Mitral Valve Replacement per 1000 Enrollees
- Asthma Discharges per 1000 Enrollees
- Back Surgery per 1000 Enrollees
- Cardiologists per 100000 Residents
- Cellulitis Discharges per 1000 Enrollees
- Cholecystectomy per 1000 Enrollees
- Congestive Heart Failure Discharges per 1000 Enrollees
- COPD Discharges per 1000 Enrollees
- Coronary Angiography per 1000 Enrollees
- Coronary Artery Bypass Grafting (CABG per 1000 Enrollees
- Coronary Artery Bypass Grafting (CABG per 1000 Enrollees
- Discharges for Ambulatory Care Sensitive Conditions per 1000 Enrollees
- Discharges for Convulsions per 1000 Enrollees
- Echocardiography per 1000 Enrollees
- Electrocardiographic Monitoring per 1000 Enrollees
- Electrophysiologists per 100000 Residents
- Electrophysiology Studies per 1000 Enrollees
- Emergency Medicine per 100000 Residents
- Endocrinologists per 100000 Residents
- Family Practitioners per 100000 Residents
- Gastroenteritis Discharges per 1000 Enrollees
- Gastroenterologists per 100000 Residents
- General Invasive Cardiologists per 100000 Residents
- General Non-Invasive Cardiologists per 100000 Residents
- General Surgeons per 100000 Residents
- Hematologists/Oncologists per 100000 Residents
- Hip Replacement per 1000 Enrollees
- Hospital beds per capita
- Hospitalization for Hip Fracture per 1000 Enrollees
- Hypertension Discharges per 1000 Enrollees
- Imaging Stress Testing per 1000 Enrollees
- Implantable Cardioverter-Defibrillator Implantation per 1000 Enrollees
- Infectious Disease Specialists per 100000 Residents
- Internists per 100000 Residents
- Interventional Cardiologists per 100000 Residents
- Kidney/Urinary Infection Discharges per 1000 Enrollees
- Knee Replacement per 1000 Enrollees
- Medical Discharges Excluding ACS Events per 1000 Enrollees

Figure 5A

- Neonatologists per 100000 Residents
- Nephrologists per 100000 Residents
- Neurologists per 100000 Residents
- Neurosurgeons per 100000 Residents
- Non-Stress Nuclear Studies per 1000 Enrollees
- Obstetrician/Gynecologists per 100000 Residents
- Ophthalmologists per 100000 Residents
- Orthopedic Surgeons per 100000 Residents
- Other Medical Specialists per 100000 Residents
- Other Pediatric Medical Specialists per 100000 Residents
- Other Pediatric Surgical Specialists per 100000 Residents
- Other Surgical or Diagnostic Specialists per 100000 Residents
- Otolaryngologists per 100000 Residents
- Pacemaker Insertion per 1000 Enrollees
- Pathologists per 100000 Residents
- Pediatricians per 100000 Residents
- Percutaneous Coronary Interventions per 1000 Enrollees
- Physical Medicine/Rehabilitation per 100000 Residents
- Physicians per 100000 Residents
- Plastic & Reconstructive Surgeons per 100000 Residents
- Primary Care Physicians per 100000 Residents
- Proportion of Aortic Valve Replacement Procedures Performed on Enrollees Age 75 and Over
- Proportion of Aortic Valve Replacement Procedures with Simultaneous CABG
- Proportion of CABG Procedures Using Internal Mammary Artery
- Proportion of Pacemakers Implanted That Were Dual Chamber Models
- Proportion of Patients Having Stress Test Prior to Revascularization
- Proportion of Patients Readmitted Within 30 Days of Initial Revascularization
- Proportion of Percutaneous Coronary Interventions With Stent
- Psychiatrists per 100000 Residents
- Pulmonologists per 100000 Residents
- Radiation Oncologists per 100000 Residents
- Radical Prostatectomy per 1000 Enrollees
- Radiologists per 100000 Residents
- Resection for Colon Cancer per 1000 Enrollees
- Rheumatologists per 100000 Residents
- Selected Specialists per 100000 Residents
- Signal-Averaged ECG per 1000 Enrollees
- Specialists per 100000 Residents
- Tilt Table Procedures per 1000 Enrollees
- Total Stress Testing per 1000 Enrollees
- Transurethral Prostatectomy for Benign Prostatic Hyperplasia per 1000 Male Enrollees
- Unallocated Cardiac Catheterization Laboratories per 100000 Residents
- Unspecified Physicians per 100000 Residents
- Urologists per 100000 Residents
- Vascular Surgeons per 100000 Residents

Figure 5B

SYSTEMS AND METHODS FOR PREDICTING HEALTHCARE RELATED FINANCIAL RISK

REFERENCE TO RELATED APPLICATIONS

This application claims the benefit of and priority to: U.S. Provisional Application No. 60/628,476, filed on Nov. 16, 2004, entitled "Healthcare Surgical and Diagnostic Event Risk Predictive Modeling Analytic System Incorporating Unwarranted Geographic Treatment Pattern Variation Data"; U.S. Provisional Application No. 60/628,504, filed on Nov. 16, 2004, entitled "Healthcare Financial Risk Predictive Modeling Analytic System Incorporating Unwarranted Geographic Treatment Pattern Variation Data"; and U.S. Provisional Application No. 60/628,212, filed on Nov. 16, 2004, entitled "Healthcare Risk Predictive Modeling Analytic System Incorporating Unwarranted Geographic Treatment Pattern Variation Data." This application is co-pending with Ser. No. 11/280,611, filed Nov. 16, 2005, and entitled "Systems and Methods for Predicting Healthcare Related Risk Events." The entire contents and teachings of the above referenced applications are incorporated herein by reference.

FIELD OF THE INVENTION

The invention relates generally to methods and systems for healthcare system analysis. More particularly, in various embodiments, the invention relates to applying predictive modeling to healthcare information to predict healthcare financial risk.

BACKGROUND

Numerous countries throughout the world are facing an unprecedented rise in healthcare costs affecting both healthcare providers and employers. One major component of healthcare costs is costs associated with surgery. Another component of healthcare costs is costs associated with diagnostics.

Healthcare predictive models have been employed that utilize actuarial models of cost predictions based on standard demographic data of patients to predict health care costs. Predictive statistical modeling is a field of data mining that utilizes statistics, machine learning, pattern recognition, and other techniques to analyze information and/or data. Other healthcare predictive models have included timing data associated with the periods when patients are examined for a particular illness to estimate costs. However, prior attempts at predictive healthcare models have focused on resource utilization, rather than the likelihood that an individual will undergo a specific surgical or diagnostic procedure.

Accordingly, there remains a widespread need for improved mechanisms to assist healthcare providers and employers to lower healthcare costs while providing superior quality of healthcare to patients. For healthcare providers such as health insurers and managed care organizations ("MCOs"), there exists a need for determining which patients are likely to present the highest risk of undergoing a surgical or diagnostic procedure, referred to as event risk, which can assist in developing strategies for managing healthcare programs.

SUMMARY OF THE INVENTION

The invention, in various embodiments, is directed to systems, methods, and/or devices relating to identifying patients who are likely to incur costs associated with healthcare. According to one feature, the invention defines certain healthcare related risk events that lead to incurring such costs. Risk events includes two broad categories; diagnostic risk events and therapeutic risk events. A diagnostic risk event includes, for example, a medical procedure performed by a healthcare professional to identify a medical condition associated with a patient. A therapeutic risk event includes, for example, a medical procedure and/or treatment performed by a healthcare professional to treat a medical condition associated with a patient. Either a therapeutic or diagnostic risk event may include a surgical risk event. A surgical risk event is any medical procedure provided by a healthcare professional for a patient involving the removal, replacement, and/or examination of an organ or tissue. A surgical risk event may also be defined as the diagnosis or treatment of an injury, deformity, or disease by manual and instrumental means.

By predicting risk events, the invention enables interested parties to establish intervention plans to mitigate the occurrence of risk events for patients. Interested parties include, for example, healthcare providers, insurers, and payors. By mitigating the occurrence of risk events, the invention mitigates the costs or financial risks associated with such risk events. Risk events and financial risks may be collectively referred to as healthcare related risk outcomes.

More particularly, the invention employs a predictive model to identify patients who are likely to incur costs associated with healthcare. The predictive model may utilize multiple factors and/or variables to predict which patients are most likely to incur the highest, lowest, or a selected range of healthcare costs by predicting which patients are likely to incur certain costly risk events. The number of risk factors utilized can be extensive and include, without limitation, patient data and geographic/healthcare systems data.

The patient data may include information such as medical claims data, pharmacy claims data, referral post hospital discharge data, healthrisk assessment and functional status data, laboratories values, pre-notification or authorization data, and other risk factor data. The geographic/healthcare system factors may include practice pattern variation data, supply-sensitive factor data, healthcare system factor data, and other geographic and healthcare system factor data. In particular, the invention advantageously utilizes unwarranted healthcare/geographical treatment pattern variation data to more accurately predict which patients are more likely in incur certain risk events. An unwarranted healthcare/geographic treatment pattern variation is any variation in treatments across different geographic regions and healthcare systems that is not caused by patient preferences or characteristics.

In one feature, the predictive model determines the most significant risk factors associated with a particular type of risk event. Once the significant factors are identified, a logistic regression model is employed to apply a weight to each significant factor based on how closely each factor correlates to a risk event. The invention applies the risk factors and associated weights to a population of patients to establish a total weight or score for each patient of the population. Based on the total weights, the invention identifies a portion of patients associated with a range of susceptibility to a particular risk event.

According to one advantage, the invention enables interested parties to predict likely healthcare costs for an upcoming period. According to certain implementations, the invention enables the projection of healthcare costs over a period of at least about 3 months, 6 months, 9 months, 12 months, or greater than about 12 months.

According to another advantage, the invention enables interested parties to take action to limit healthcare costs by, for example, providing early intervention plans to patients and/or interested parties that prevent or mitigate the occurrence of risk events. The prevention of certain risk events may encourage interested parties such as healthcare insurers to pay for or cover the cost of such early intervention programs.

In various embodiments, the invention provides, without limitation, mathematical models, algorithms, methods, systems, devices, computer program codes, and computer readable mediums for performing the above predictive models to identify healthcare related risk outcomes.

In one aspect, the invention employs a software application running on a computer system for predicting healthcare related financial risks. The software application may perform functions including: accessing patient data associated with one or more patients; accessing geographic and healthcare system data; filtering the patient data, geographic data, and healthcare system data into clean data; and applying a predictive model to the clean data to generate patient profile data and to identify a portion of the patients associated with a range of predicted financial risk.

In one feature, the invention categorizes one or more patients into one or more clinical segments. The segments may be based on preference sensitive conditions, chronic disease, or large medical cases not associated with chronic disease. In another feature, the invention applies the predictive risk model to each clinical segment and/or uses the segments to apply the predictive model.

In one configuration, the invention generates one or more facts based on the clean data. In a further feature, the invention reports the portion of patients susceptible to one or more risk events to a healthcare provider. In another feature, the invention generates suggested intervention plans for one or more patients based on each patient's susceptibility to a risk event.

The patient data may include patient claims data and patient non-claims data. The patient claims data may include medical claims data and/or pharmacy claims data. The patient non-claims data may include referral data, functional status data, laboratory values, patient risk factors, demographics, disease burden, and/or disease complications. The geographic data may include geographic practice pattern variables and/or unwarranted geographic treatment pattern variations. The healthcare system data may include unwarranted healthcare system treatment pattern variations.

In one configuration, the invention filters the patient data, geographic data, and healthcare system data into clean data by importing patient data files, mapping patient data into standard formats, processing adjustments and duplicates, checking patient data parameters against internal and external normal parameters, identifying and correcting data errors, and creating a table to link patient data to unique patient identifiers.

In another configuration, the predictive model includes: separating patient data into a first and second data set; evaluating regressively one or more risk factors in the first data set to determine weights associated with significant risk factors; and applying the weights for each significant risk factor to the second data set to validate the prediction risk model performance. In one embodiment, the predictive model evaluates regressively one or more risk factors in the second data set to determine weights associated with significant risk factors. The predictive model then compares the weights of risk factors of the first data set with the weights of the risk factors of the second data set.

In another feature, the invention includes applying, without limitation, a linear regression model, a non-linear regression model, a logistic regression model, a Bayesian network model, a Markov model, or a propensity score to evaluate the risk factors. In one configuration, the invention adds the weights of the risk factors associated with one or more patients to generate risk totals associated with the one or more patients. The invention identifies a portion of the patients susceptible to one or more risk events by identifying a portion of the one or more patients with the highest risk totals. A weight may include a beta weight. A risk score and/or risk total may be derived from the beta weight. The risk score may include a value in the range of 0 to 1. The weight may include a cost associated with risk factor.

In one feature, validating includes applying a best-fit test or goodness-of-fit measure. In another feature, the invention refines and validates the risk predictive model by comparing a first portion of the patient profile data with a second portion of the patient profile data. The refining and validating process may include dividing the patient profile into a model development data set and a model validation data set and applying weights to the model development data set to profile the model validation set. The data may include one or more variables.

In one configuration, the model development data may include patient claims data associated with a first period of time and the model validation data is associated with a second period of time.

In another configuration, the portion of the patients susceptible to the one or more risk events may include a selected percentage of the patients that are most susceptible to the one or more risk events.

In a further configuration, the portion of the patients susceptible to the one or more risk events may include a selected percentage of the patients that represent patient that are least susceptible to the one or more risk events.

In yet a further configuration, the portion of patients susceptible to the one or more risk events may include a portion of the patients representing a selected spectrum of susceptibility to the one or more risk events.

The invention will now be described with reference to various illustrative embodiments.

BRIEF DESCRIPTION OF THE DRAWINGS

The foregoing and other objects, features, advantages, and illustrative embodiments of the invention will now be described with reference to the following drawings in which like reference designations refer to the same parts throughout the different views. These drawings are not necessarily to scale, emphasis instead being placed upon illustrating principles of the invention.

FIGS. 5A and 5B include an exemplary list of selected geographic practice pattern variables according to an illustrative embodiment of the invention.

DESCRIPTION OF ILLUSTRATIVE EMBODIMENTS

Figure 1:
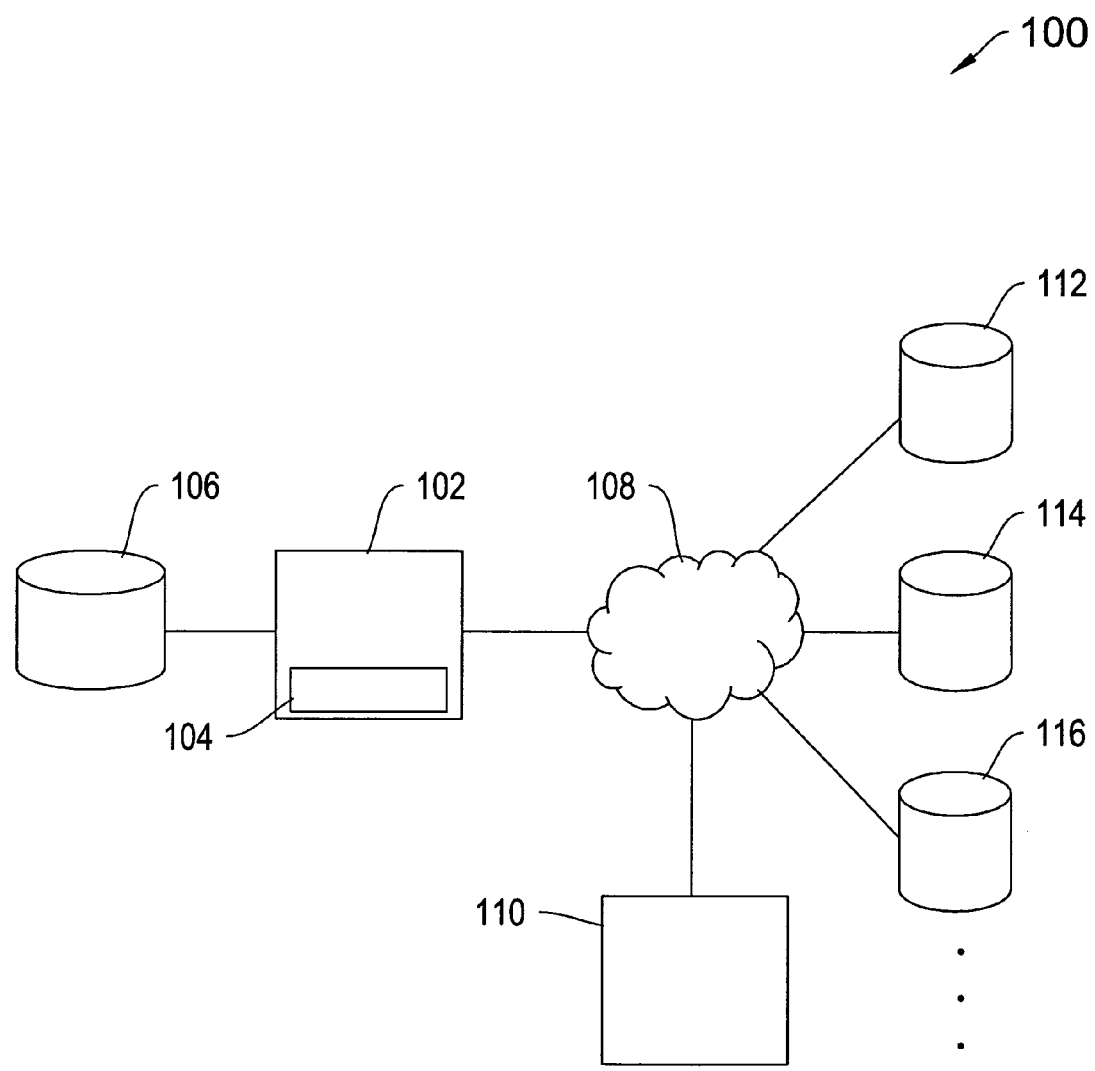
FIG. 1 is a conceptual block diagram of a healthcare risk predictive modeling analytic system according to an illustrative embodiment of the invention.

As described above in the summary, the invention is generally directed to systems and methods that identify patients who have a predicted susceptibility and/or level of risk (e.g., more risk or less risk or a selected range of risk) to certain event risks and/or are associated with certain levels of financial risk, thereby facilitating the establishment of intervention plans to mitigate the healthcare event risks for patients and financial risks for patients and/or healthcare providers.

In one embodiment, predictive modeling is employed because it has the potential to reduce healthcare costs and/or spending while assisting patients by helping MCOs, insurers, or other providers identify patients who are most likely to incur future surgical and/or diagnostic events, and target specialized interventions to assist such existing patients, or new enrollees. Predictive modeling may also allow MCOs, insurers, or other providers to identify which patients will likely consume the most resources in the future as a result of such event risks and/or financial risks. Predictive modeling may further enable healthcare providers to identify high risk patients, and get interventions to them, as medical, biotech and drug treatments have grown more sophisticated and expensive.

In another embodiment, the invention is directed to systems and methods relating to surgical and diagnostic event risk predictive modeling (herein surgical, treatment, and diagnostic procedures may be referred to as events). In one feature, a system according to the invention assists in the determination of event risk—the risk of undergoing a surgical or diagnostic procedure, not the risk of adverse outcomes from the procedure—within a defined patient population. In another feature, a system according to the invention assists in the determination of financial risk to a healthcare provider associated with a patient population.

In a further embodiment, the invention helps identify individuals within a population who are at the highest risk of incurring such event risks, preferably within about a 3-9 month period. In yet another embodiment, a system according to the invention assists in the determination of diagnostic event risk—the risk of undergoing any diagnostic procedure (such as, for example, a Magnetic Resonance Imaging study; a coronary angiography catheterization; or an echocardiogram of the heart), not the risk of adverse outcomes from the procedure—within a defined patient population, and helps identify individuals within a population who are at the highest risk of incurring such diagnostic event risks, preferably within about a 3-9 month period.

The invention may also be applied to predicting the risk of any surgical procedure including, but not limited to, those associated with the knees, the hip, the back, uterine fibroids and uterine bleeding, and cardiac event risks (including, for example, coronary artery bypass graft ("CABG"), and Percutaneous Transluminal Coronary Angioplasty ("PTCA") or other modalities of catheter based treatments of the coronary arteries).

In one embodiment, the invention employs statistical predictive modeling and clinical segmentation analytics to combine data associated with unwarranted geographic treatment pattern variations with relevant patient claim and non-claim information to determine future event risks and/or financial risks (collectively referred to as "predicted risk outcomes") of the aforementioned types within patient populations. According to another feature, the invention also identifies individuals within a population who are at the highest risk of incurring such event risks or who are susceptible to incurring, generating, or otherwise experiencing a certain level of healthcare costs. This identification enables healthcare organizations to engage in intervention and health coaching of high risk individuals to lower their event risks and/or financial risks or costs.

While prior attempts at predictive healthcare models have focused on resource utilization, one configuration of the invention includes an analysis of the likelihood that an individual will undergo a specific surgical, treatment, or diagnostic procedure. According to one advantage, the systems and methods of the invention recognize the importance of unwarranted geographic treatment pattern variation data, and rely upon various information including, without limitation, medical research, a given patient's medical claims experience, and non-claims factors to identify relationships between healthcare utilization and event risks and/or financial risks.

FIG. 1 is a conceptual block diagram of a healthcare risk predictive modeling analytic system 100 according to an illustrative embodiment of the invention. The analytic system 100 includes computer system 102, local healthcare database 106, network 108, remote information system 110, and remote healthcare databases 112, 114, and 116. The computer system 102 also includes predictive risk modeling application 104.

Figure 2:
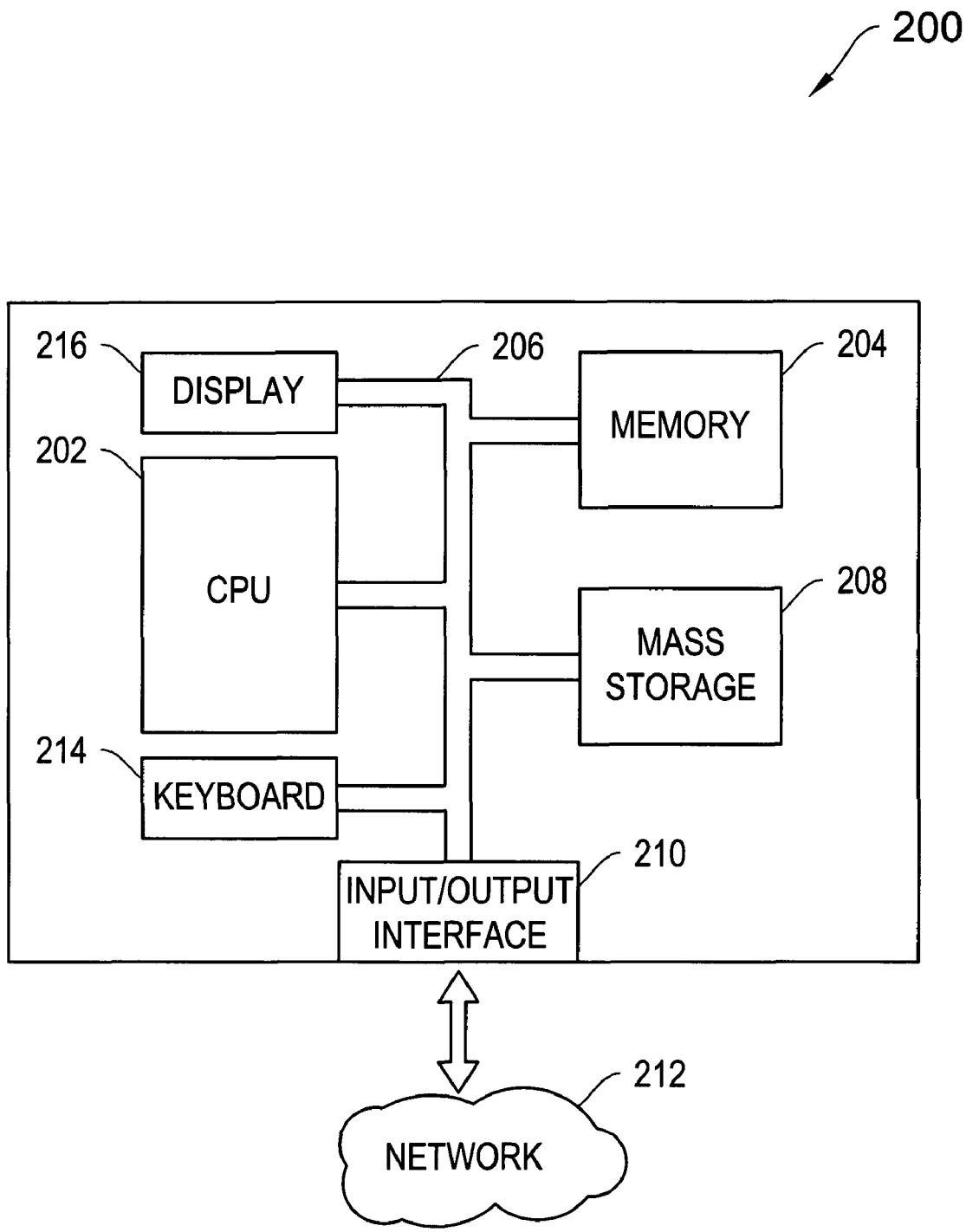
FIG. 2 is a functional block diagram of a computer for performing a predictive analysis according to an illustrative embodiment of the invention.

FIG. 2 shows a functional block diagram of general purpose computer system 200 for performing the functions of the computer 102 according to an illustrative embodiment of the invention. The exemplary computer system 200 includes a central processing unit (CPU) 202, a memory 204, and an interconnect bus 206. The CPU 202 may include a single microprocessor or a plurality of microprocessors for configuring computer system 200 as a multi-processor system. The memory 204 illustratively includes a main memory and a read only memory. The computer 200 also includes the mass storage device 208 having, for example, various disk drives, tape drives, etc. The main memory 204 also includes dynamic random access memory (DRAM) and high-speed cache memory. In operation and use, the main memory 204 stores at least portions of instructions and data for execution by the CPU 202.

The mass storage 208 may include one or more magnetic disk or tape drives or optical disk drives, for storing data and instructions for use by the CPU 202. At least one component of the mass storage system 208, preferably in the form of a disk drive or tape drive, stores the database used for processing the predictive modeling of system 100 of the invention. The mass storage system 208 may also include one or more drives for various portable media, such as a floppy disk, a compact disc read only memory (CD-ROM), or an integrated circuit non-volatile memory adapter (i.e. PC-MCIA adapter) to input and output data and code to and from the computer system 200.

The computer system 200 may also include one or more input/output interfaces for communications, shown by way of example, as interface 210 for data communications via the network 212. The data interface 210 may be a modem, an Ethernet card or any other suitable data communications device. To provide the functions of a computer 102 according to FIG. 1, the data interface 210 may provide a relatively high-speed link to a network 212, such as an intranet, internet, or the Internet, either directly or through an another external interface. The communication link to the network 212 may be, for example, optical, wired, or wireless (e.g., via satellite or cellular network). Alternatively, the computer system 200 may include a mainframe or other type of host computer system capable of Web-based communications via the network 212.

The computer system 200 also includes suitable input/output ports or may use the interconnect bus 206 for interconnection with a local display 216 and keyboard 214 or the like serving as a local user interface for programming and/or data entry, retrieval, or manipulation purposes. Alternatively, server operations personnel may interact with the system 200 for controlling and/or programming the system from remote terminal devices via the network 212.

The computer system 200 may run a variety of application programs and store associated data in a database of mass storage system 208. One or more such applications may enable the receipt and delivery of messages to enable operation as a server, for implementing server functions relating to predicting risk event and/or financial risks using application 104 of FIG. 1.

The components contained in the computer system 200 are those typically found in general purpose computer systems used as servers, workstations, personal computers, network terminals, portable devices, and the like. In fact, these components are intended to represent a broad category of such computer components that are well known in the art. Certain aspects of the invention may relate to the software elements, such as the executable code and database for the server functions of the predictive risk modeling application 104.

Returning to FIG. 1, the predictive risk modeling application 104, in various embodiments, may combine predictive statistical modeling with clinical segmentation analytics to determine future risk of having identified surgeries or diagnostic procedures within a defined population and/or set of patients, and/or the associated financial risks.

Figure 3:
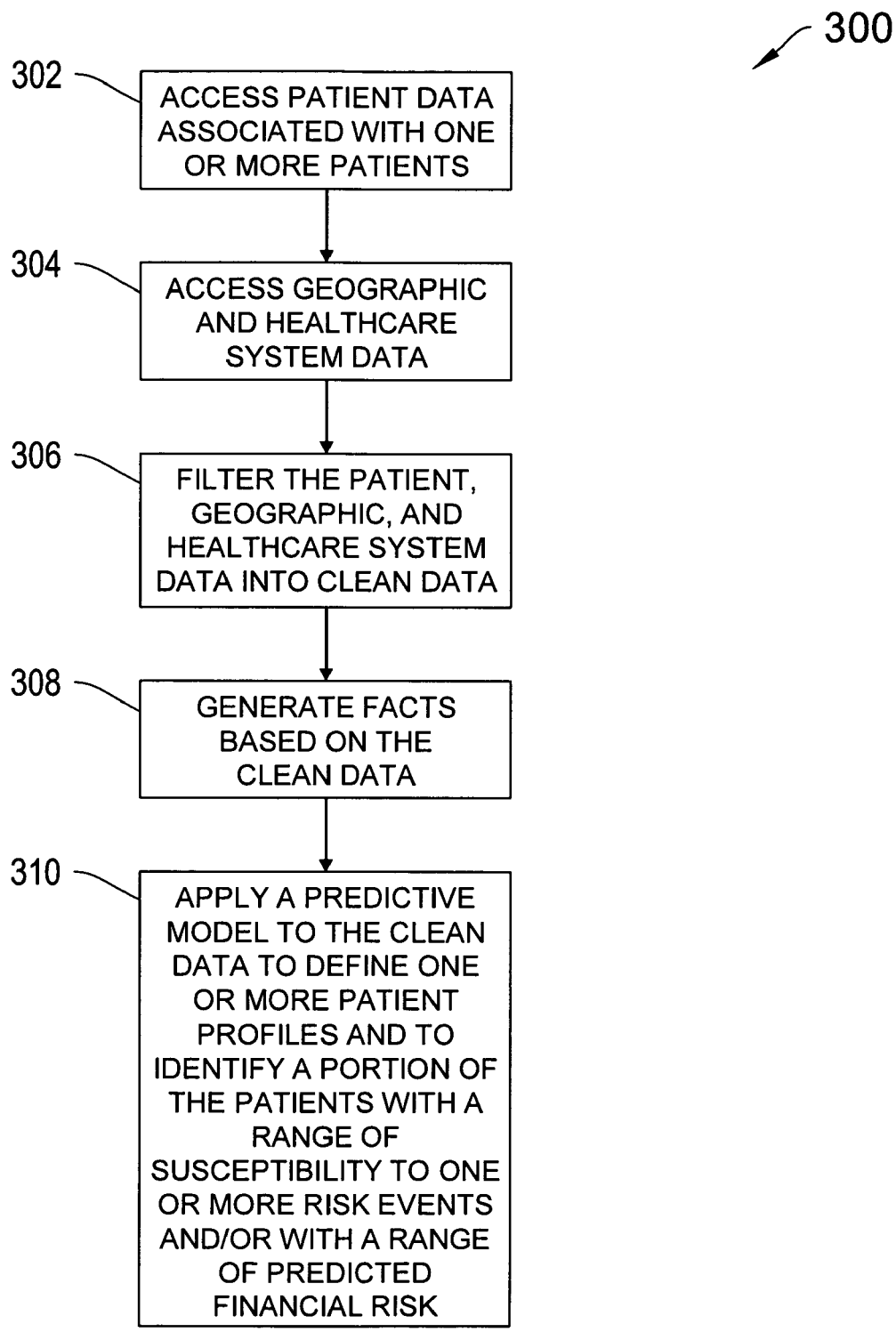
FIG. 3 is a flow diagram of an exemplary healthcare system risk analysis process according to an illustrative embodiment of the invention.
Figure 4:
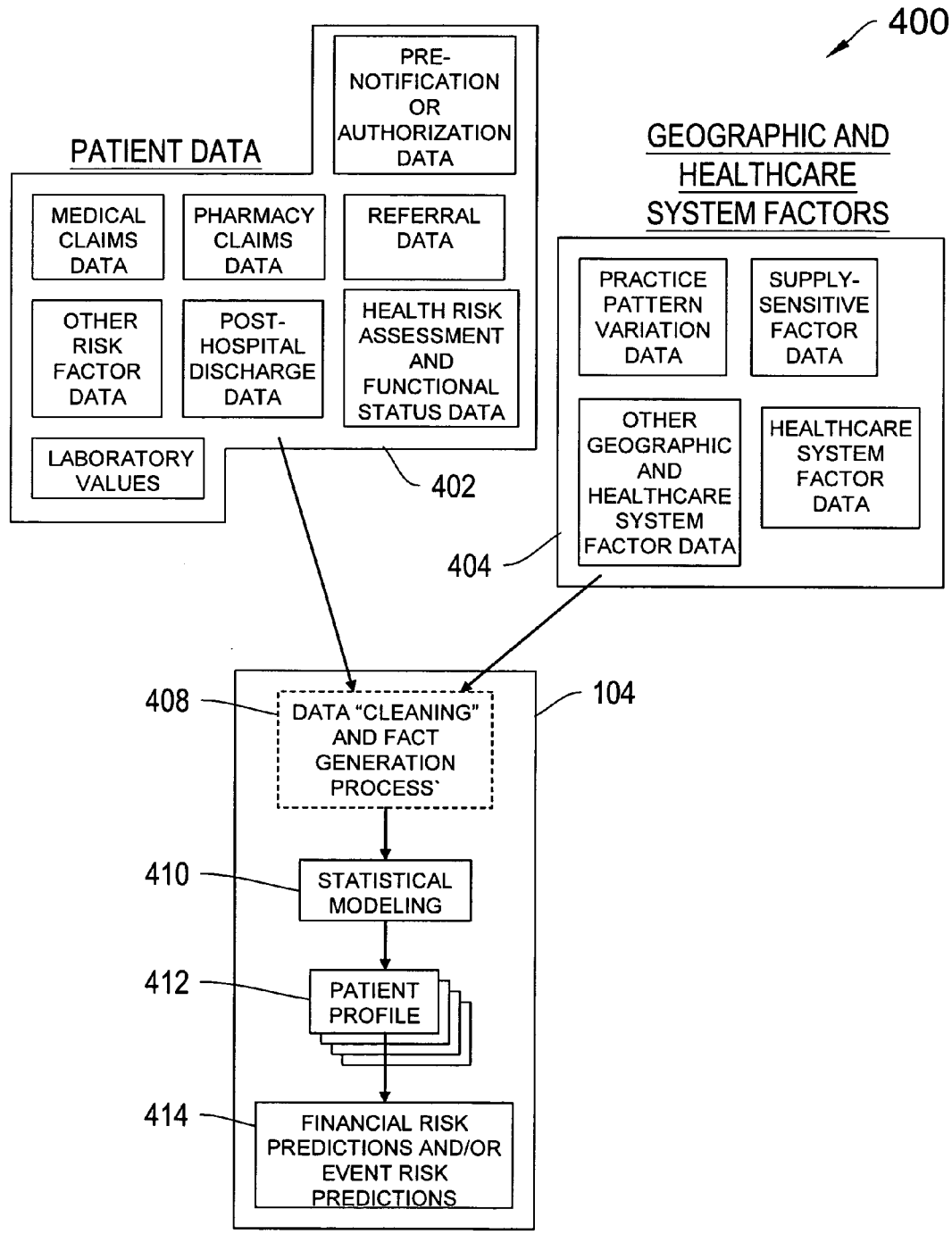
FIG. 4 is a conceptual block diagram of the healthcare risk analysis process according to an illustrative embodiment of the invention.

FIGS. 3 and 4 are a flow and conceptual diagrams, respectively, of an exemplary healthcare system risk analysis process 300 and system 400 according to an illustrative embodiment of the invention. In operation in certain embodiments, the software application 104 performs the following. The application 104 accesses and/or retrieves patient data 402 associated with one or more patients (Step 302). The patient data 402 may reside within an internal database 208, local database 106, or a remote database 112, 114, and 116. The remote databases 112, 114, and 116 may be accessible via a communications network 108 including, for example, any one or combination of the Internet, an internet, an intranet, a local area network (LAN), wide area network (WAN), a wireless network, and the public switched telephone network (PSTN). Each of the remote databases 112, 114, and 116 may be associated with a public and/or private healthcare database including patient specific information, general healthcare information, general demographic information, and/or other information relevant to the financial and/or risk event analysis process 300.

The application 104 may also access and/or retrieve geographic and healthcare system data 404 (Step 304). Then, the application 104 filters the patient, geographic, and healthcare system data into clean data using a data cleaning/fact generation component 408 (Step 306). Based on the clean data, the application 104 generates one or more facts using the data cleaning/fact generation component 408 (Step 308). Then, the application 104 applies a predictive statistical model 412 to the clean data to generate and/or define patient profile data and/or to identify a portion of the patients associated with a range of predicted financial risk and/or to identify a portion of the patients with a range of susceptibility to one or more risk events (Step 310). The application 104 may output the financial risk predictions and/or risk event predictions 414 in the form of a data file that may be delivered to a local user interface and/or display 216 or to a remote information system 110 for further processing and/or viewing. In one embodiment, the clean data processed by the prediction model includes the facts generated from the clean data in Step 308 and/or any information that can be correlated to a predicted risk outcome.

In further illustrative embodiments, the application 104 also identifies individuals within such a population who are at the highest risk of incurring risk events. According to one advantage, the application 104 applies predictive statistical modeling, in combination with clinical segmentation analytics, to patient data, and also takes into account geographic factors. In one embodiment, the invention enables the aforementioned determination for about a 3-9 month period following the determination. In other embodiments, other periods may be used, such as, and without limitation, about a 1-3 month period, about a 1-6 month period, about a 1-9 month period, about a 1-12 month period, and greater than about 12 month period following the determination. In another illustrative embodiment, the application 104 performs clinical segmentation across patients exhibiting one or more of the following: preference sensitive conditions; chronic diseases; and large medical cases that do not fall into any chronic disease category. Chronic diseases may include, but are not limited to, asthma, chronic obstructive pulmonary disease ("COPD"), coronary artery disease ("CAD"), congestive heart failure ("CHF"), and diabetes. Clinical segmentation is described in greater detail below.

As shown in FIG. 4, the various categories of data that may be used by the application 104 of predictive modeling analytic system 100 include, but are not limited to, the following: patient data 402 including, e.g., claims-related data and non-claims related data; and geographic and timely medical research data on geographic and healthcare system factors 404 including, e.g., healthcare system factor data, unwarranted geographic treatment pattern variation data, and data addressing clinical care gaps in healthcare systems patient care delivery.

Clinical care gaps include gaps in patient care where a patient has not received tests, medications, or treatments in accordance with established evidence-based clinical guidelines specific to a patient's condition, or where a patient is receiving tests, treatments or medications in contrast to established evidence-based clinical guidelines. Clinical care gaps are used to identify unwarranted variation in the area of effective care. Health care system factor data includes information about the health care system where an individual receives care, e.g., geographic area, a hospital referral region (HRR), and/or the hospital system (a hospital and the physicians who practice in it). These factors may include the number of hospital beds per capita, number of specialists per capita, and/or diagnostic testing intensity associated with the health care system. Health care system factor data has been shown to be a strong determinant of the number of supply sensitive services a patient receives.

Patient claims data may include, but are not limited to, the following classes of data: medical claims data and pharmacy claims data. Patient non-claims data may include, but are not limited to, referral data, pre-notification or authorization data, post-hospital discharge data, health risk assessment and functional status data, laboratory values (such as, for example, prostate-specific antigen (PSA) values), and other patient risk factors that include, but are not limited to, demographics, disease burden, and disease complications.

FIGS. 5A and 5B include an exemplary list of selected geographic and/or healthcare practice pattern variables according to an illustrative embodiment of the invention. Geographic and/or healthcare practice pattern variables for which geographic rates of practice pattern variation are analyzed in the model include, but are not limited to, those provided in FIGS. 5A and 5B. Unwarranted healthcare system and geographic treatment pattern variation is defined as variation in treatments across different healthcare systems and geographic regions that is not driven by patient preferences or characteristics. Patient demographics may include, but are not limited to, a patient's unique member identification, date of birth, sex, enrollment and membership information, and geographic data such as ZIP code, Hospital Service Area ("HSA"), and/or Hospital Referral Region ("HRR"). Pharmacy claims data may be maintained, for example, at drug class or NDC-level, with groupings by class; this data may include, but is not limited to, number of dispensed prescriptions; days supply; measures of adherence; and most recent fill date.

The application 104, according to certain illustrative embodiments, employs statistical modeling to capture relevant relationships based on a patient's history. According to a further embodiment, the application 104 also incorporates timely medical research on geographic and healthcare system factors 404 into the healthcare event risk and/or financial risk predictive model, which yields results that are both predictive and clinically relevant. In one preferred illustrative embodiment, the timely medical research data 404 includes clinical research data supported by institutions such as the Foundation for Informed Decision Making, Dartmouth Center for the Evaluative Clinical Sciences, Harvard Medical School, or Maine Medical Center's Center for Outcomes Research and Evaluation which may reside, for example, within one or more databases such as databases 112, 114, and 116.

The incorporation of unwarranted geographic and healthcare system treatment pattern variation data into the risk event and/or financial risk model of the application 104 allows interested parties such as insurers, healthcare plans, employers, or other providers or payors to identify and reduce unwarranted variations in the real-world delivery of healthcare, and to identify a higher likelihood of successful health coaching opportunities. According to one illustrative embodiment, the application 104 incorporates research on disease burden, geographic practice patterns, and supply-sensitive factors into the risk event and/or financial risk models. By way of example, supply-sensitive factors may include, but are not limited to, admission and re-admission frequency; total hospital days; frequency of emergency room visits; frequency of physician visits; date of most recent encounter; number of unique providers seen; and visit frequency among: PCPs, nurse practitioners, chiropractors, OB/GYNs, specialists overall, and other provider types; and relative value units ("RVU"), total and sub-group, which may be used as a standardized resource utilization measure instead of cost.

Prospective modeling employed by the illustrative application 104 may be used to predict risk events and/or financial cost for a given time period based on risk factors identified in a prior time period. In one embodiment, that application 104 requires members and/or patients used in the modeling process to have continuous eligibility in a healthcare system for both time periods. Such risk factors may include incurred costs. Since the values of incurred costs do not tend to follow a linear pattern, costs may be transformed using data transformation factors within the statistical modeling component 412 of the application 104 that include, for example, the natural logarithm. Various conventional statistical modeling systems may be employed in the application 104, including, but not limited to, Markov and Bayesian statistical modeling systems. The application 104 may be implemented with and applied to computer-based modeling using any suitable computer language. In one illustrative embodiment, the computer language used is SAS. Other computer languages may include, without limitation, C, C++, JAVA®, COBAL, BASIC, HTML, XML, SGML, and like computer languages.

Preferably, patient data 402 includes claim and non-claim data and patient-related risk factors. The patient data 402 may be processed including geographic factors in the risk event and/or financial risk predictive model of the application 104 as shown in FIG. 4. These patient-related risk factors may include, but may not be limited to, age; gender; significant medical events; chronic conditions including, but not limited to, asthma, chronic obstructive pulmonary disease ("COPD"), coronary artery disease ("CAD"), congestive heart failure ("CHF"), and diabetes; co-morbidities; complications; utilization; clinical diagnostic groupings; code groupings; procedural groupings, pharmaceutical claims, and geographic region. According to an illustrative embodiment, the data for the risk event and/or financial risk predictive model of the application 104 may then be subjected to a data cleaning process, and may also be subjected to a process to identify and categorize relevant facts and relationships among facts (a fact generation process, described below) by data cleaning/fact generation component 408, to create one or more patient profiles 410.

Figure 6:
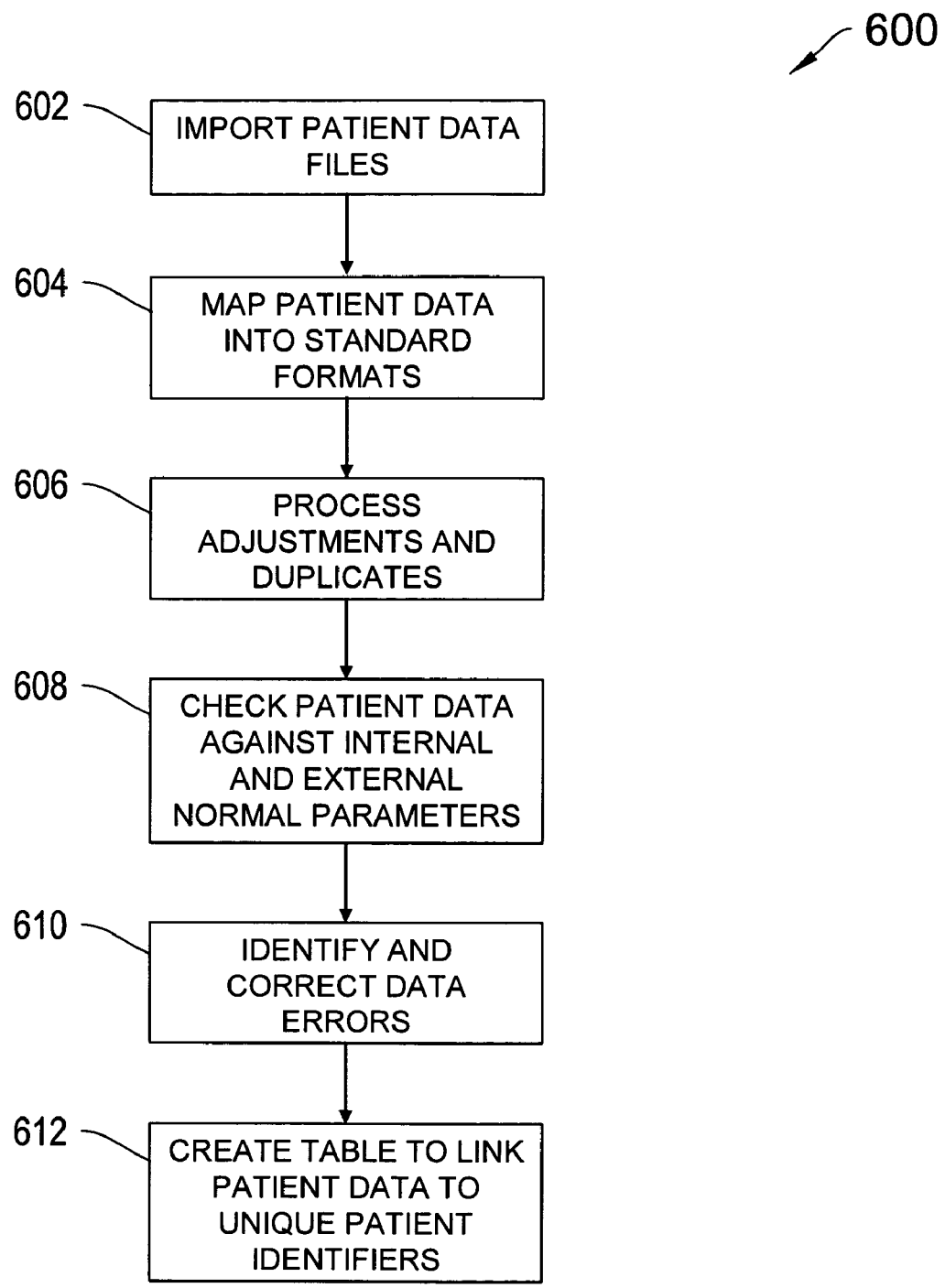
FIG. 6 is an exemplary flow diagram of an exemplary data cleaning process according to an illustrative embodiment of the invention.

FIG. 6 is a flow diagram of an exemplary data cleaning process 600 according to an illustrative embodiment of the invention. In this illustrative embodiment, data cleaning may include, for example, one or more of: (1) Importing client data files (Step 602); (2) Mapping client data to standard formats (Step 604); (3) Processing adjustments and duplicates (Step 606); (4) Checking client data against internal and external norms (Step 608); (5) Identifying and correcting data errors (Step 610); and (6) creating a patient-level system of tables to link client data to unique patient identifiers (Step 612). In one embodiment, the application 104 excludes members with certain disease states, trauma, dialysis or heart transplants from the predictive model because such procedures may entail high financial risks.

As noted above, data may also be subject to a fact generation process in connection with preparing a patient profile. This is a process aimed at consistently extracting and employing clinical, financial, utilization and/or individual information from healthcare data.

The facts (including relationships among facts) resulting from this process can be defined at multiple levels, such as:

First-level facts—these are the most basic facts, and are used to identify certain types of claims (e.g., claims pertaining to an asthma diagnosis). They are based directly on clinical codes (such as CPT4, ICD9, revenue codes, and specialty codes). For example, cardiac catheterization (CATH), Echo, and Percutaneous Transluminal Coronary Angioplasty (PTCA) are all first-level procedure facts.

Second—or higher-level facts—these are based on Boolean (e.g., AND, OR) association of first- or other lower-level facts. For example, left ventricular ejection fraction (LVEF) is a higher-level procedure fact based on lower-level CATH, Echo and PTCA facts.

Complex facts—these are based on an association of facts through complex logical relationships. Identification facts are an example of complex facts, as is the final output leading to a risk event and/or financial risk prediction fact.

In one preferable embodiment, a risk predictive modeling analytic system 100 includes, but is not limited to, approximately 1500 such facts. The facts identified in the analysis process can be used in the application 104 for various purposes, such as:

Development and refinement of the statistical model;
Reporting of event risk and/or financial risk predictions; and/or
Generating suggested intervention campaigns based on event risk and/or financial risk predictions.

In this illustrative embodiment, the patient profile data 410 resulting from this process of data cleaning and fact generation is then fed into the predictive risk statistical modeling component 412 of the application 104. At least one data file 410 is separated (randomly or otherwise) into two data sets. The first set is used for model development and each potential data point/risk factor ("risk factor") is evaluated against client specific data. In one embodiment, a stepwise linear regression is used to filter out non-significant risk factors. In another embodiment, a non-linear regression model is used. The resulting estimates and/or, for example, weights, for each significant risk factor are applied to the second data set to validate the model's performance. Various conventional validation and "goodness of fit" tests may be employed. In one embodiment, model validation and goodness of fit tests are based on measures published by the Society of Actuaries (such as *A Comparative Analysis of Methods of Health Risk Assessment*, Daniel L., Alice Rosenblatt, Deborah A. Taira, et. al., Schaumburg, Ill., Society of Actuaries, 1996).

In one embodiment, the predictive modeling of the application 104 employs surgery indicators that have occurred about 3-15 months before the study date. This eliminates about 3 months before surgery to account for claims lag as well as the likely inability to intervene effectively in such a period before surgery.

The predictive model of the application 104 may also be refined and validated using one or more geographic factors such as clinical care gaps and geographic rates of practice pattern variation (see examples in FIGS. 5A and 5B), including various supply-sensitive factors described above. This population-specific data captures local practice patterns and the capacity of the acute care sector in the client's geographic regions that result in variations in the delivery of healthcare. Each model may be reviewed to incorporate additional clinical criteria and revisions to the model based on additional data, which may include timely medical research data 404. In one preferred embodiment, the model is reviewed quarterly. In other embodiments, the model is reviewed and updated monthly, fortnightly, weekly, or daily to incorporate additional clinical criteria and revisions to the model based on additional data.

In one embodiment, the following example of model development is employed. The model includes a split sample methodology wherein 50% of the profile data 410 is randomly selected for a model development sample and the other 50% of the data is selected for a model validation sample. A model is then developed that uses patient data 402 and geographic and healthcare system factor information 404 for a first period (such as 3-15 months) represented in the profile data 410 of the development sample to identify data points/risk factors associated with risk events and/or financial costs in a second period represented in the profile data 410 (such as the next 3 to 9 months). In an illustrative embodiment, the model used includes a logistic regression. In another, the model used includes a propensity score. Other models may also be used. Numerous variables may be used in developing the model, including without limitation age, gender, log transformed cost for the first period, number of specialist visits, primary care capacity, flags for conditions such as renal disease (not on dialysis), Rheumatologic disease, Cancer (non-metastatic), and treatment with anti-depressants, Ca+ channel blockers, ACE inhibitors, diuretics, anti-anginals, anti-anxiety medications, and cardiac glycosides. In one embodiment, the operating characteristics of the development data set are measured using $R^2$ metrics. For example, in one embodiment, the operating characteristics of the development data set are in the range $R^2=0.34-0.45$.

The predictive value of the model may be validated by applying beta weights developed from the model development sample to profile data from the validation sample, calculating predicted likely risk events and/or financial cost in a second period represented in this validation sample data based on information from a first period represented in the data, and comparing the predicted risk events and/or financial costs to the actual surgical or diagnostic events and/or actual healthcare costs experienced in the second period. In one embodiment, the operating characteristics of the validation data set are measured using ROC metrics. In one embodiment, the operating characteristics of the validation data set are in the range $R^2=0.33-0.44$.

Clinical Segmentation

According to a further illustrative embodiment, the application 104 incorporates clinical segmentation into the predictive statistical model component 412. In one embodiment, the application 104 performs clinical segmentation across the following categories: preference sensitive conditions; chronic disease; and large medical cases that do not fall into chronic disease categories. This segmentation can be used to identify information about the individuals' disease conditions and comorbidities, effective care opportunities and utilization profiles. By way of example, comorbidities include, but are not limited to, such conditions as AIDS, asthma, ischemic heart disease, chronic heart failure, diabetes, depression, hypertension, and other conditions. Effective care opportunities include, but are not limited to, pneumonia vaccination; influenza vaccination; controller medication in asthma; lipid profile; microalbuminuria testing; HgbA1C testing; diabetic eye exam; CAD/CHF beta blocker treatment; follow-up care; and other measures.

The application 104 may, for example, complete an extensive statistical analysis within each of these categories to predict future surgical or diagnostic events, or future financial costs/expenses. In one embodiment, the application 104 identifies the top about 10% of patients that represent the predicted highest impactable event risk, highest financial risk to the health plan or other payor, and/or the highest level of cost to the health plan or other payor. Within this about 10% the application 104 segments the top about 4% for highest level intensity of interventions. According to other embodiments, the application 104 segments the top about 1%, 2%, 3%, 5%, 6%, 7%, 8%, or 9% for highest level intensity of interventions. In a similar fashion, the application 104 may also segment the lowest about 1%, 2%, 3%, 4%, 5%, 6%, 7%, 8%, 9% or 10% of predicted impactable event risk and/or financial cost for lowest level intensity of interventions.

Preference Sensitive Conditions ("PSCs")

PSCs typically involve conditions where the patient has some choice of the treatment and/or action to address a medical condition, e.g., elective surgery. The application 104 may create a monthly or other period-based prediction of members that are in a "decision window" for a significant surgical or diagnostic event, or for a significant cost. These files may be revised monthly or on another periodic basis to capture the most current data on members and/or patients. (Patients with PSCs may represent, for example, 15-20% of members and 25-40% of total medical costs, with the highest risk members in this category representing excellent opportunities for health coaching and management.)

Chronic Diseases

In one preferred embodiment, the application 104 identifies patients with one of five chronic diseases: asthma, chronic obstructive pulmonary disease ("COPD"), coronary artery disease ("CAD"), congestive heart failure ("CHF"), and diabetes. In certain embodiments, these diseases may be selected because these five disease states present the greatest opportunity for intervention and reduction in unwarranted variation that can reduce medical cost while improving the quality of patient care.

Large Medical Cases

The application 104 may also provide event risk and/or financial cost estimates of those members within large medical cases that are not members of chronic disease categories. In an illustrative embodiment, these may include, for example, patients with otherwise non-identified cancers. For example, in one illustrative embodiment, large cases may be identified by Clinical Complication Scores ("CCS"), a methodology developed and continuously updated by the Agency for Healthcare Research and Quality ("AHRQ").

Building the Member Profile

In one embodiment, the results of the application 104's statistical modeling and clinical segmentation may include, but are not limited to, individual-level records that may include, for example, event risks and/or financial risks, key drivers of utilization, clinical care gaps, acute clinical events, and the probability of facing discrete Preference Sensitive Condition events. Information in each member profile may then be used to further segment members within high-risk groups. This further segmentation may be used to direct specific interventions for each member and/or patient.

In one embodiment, the application 104 uses six primary factors: excessive or unneeded hospitalizations; unneeded surgeries; clinical care gaps; overuse of emergency room service; overuse of high-cost pharmaceuticals; and under-use of appropriate preventive pharmaceuticals (condition-specific) to segment each member by their costs and utilization in each of the clinical segmentation categories mentioned above. This allows for effective member interventions across categories (e.g., interventions to reduce potential hospitalizations should be managed differently for members who have extremely high utilization of chemotherapy and other oncology drugs). Thus, the application 104 can allow for impactable financial and/or event opportunities, such as clinical opportunities. In one embodiment, the application 104 uses a combination of clinical trials and observational data to identify these opportunities.

In the application 104, an individual's predicted event risks and/or financial risks may be combined with expected results from specific, proven interventions (e.g., telephonic, mailing, others) and a healthcare organization's specific goals for the program (e.g., to reduce costs, improve Health Plan Employer Data and Information Set ("HEDIS") scores, reduce absenteeism).

One product of the application 104 may be a risk score for future predicted event risks and/or financial costs. The risk score may be presented as a percentage likelihood of event risk and/or cost in a defined period of time (e.g., a 3-9 month period in the future). Event risks and/or financial risks may be established by a predictive model of the application 104 to a range between 0 to 100%. In addition to producing a risk score for future risk events and/or costs, the application 104 may identify key points in the care process that can be used as 'leverage points' to change expected event risks and/or financial costs. These may include information about recent utilization (e.g., consultations to specialists, emergency room admissions, hospitalizations, etc.). This information may be used in care management outreach efforts.

The application 104 may also identify key selected effective care opportunities for the chronic population. Effective care opportunities (also known as "evidence based medicine") include interventions that are of known clinical effectiveness. When systematically applied, they reduce morbidity, mortality and costs. These interventions include use of specific preventive services (e.g., diabetic retinal exam) and pharmaceutical interventions (e.g., lipid lowering agents in patient with coronary artery disease). These care opportunities may be incorporated as individual and total patient clinical scores (weighted by risk) into the patient level output and that may be sent, for example, to a health plan provider or other payor.

Based on the analysis allowed by the predictive statistical model 412 of the application 104, a database of actionable information may be created such as database 208 and/or 106. In one embodiment, such actionable information may be accessed by call centers staffed by healthcare professionals such as licensed RNs, dieticians, and other clinicians to support outbound interventions to better manage high event risk and/or high cost individuals for managed care organizations. The actionable information may be stored within a database of information system 110 among other databases.

Different embodiments of the predictive modeling application 104 described herein may be implemented as computer software, hardware, or a combination of software and hardware. In certain embodiments, patient population profile information, risk event predictions, and financial risk predictions may be displayed and/or outputted to a computer graphical user interface ("GUI") such as display 216 for user viewing, or outputted to another system such as information system 110 for further processing.

Figure 7:
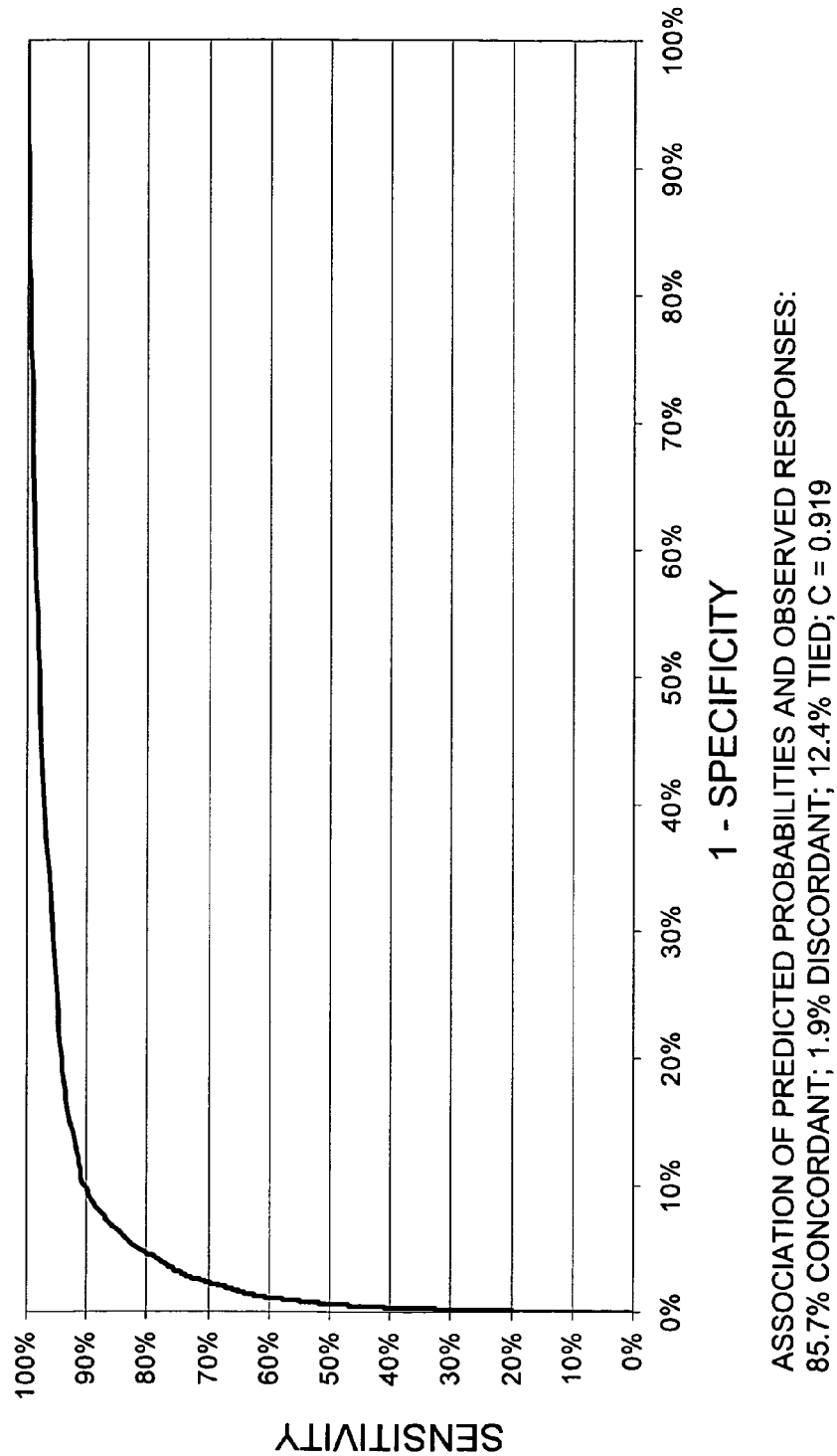
FIG. 7 is an exemplary receiver-operating characteristic (ROC) curve of sensitivity versus specificity according to an illustrative embodiment of the invention.
Figure 8:
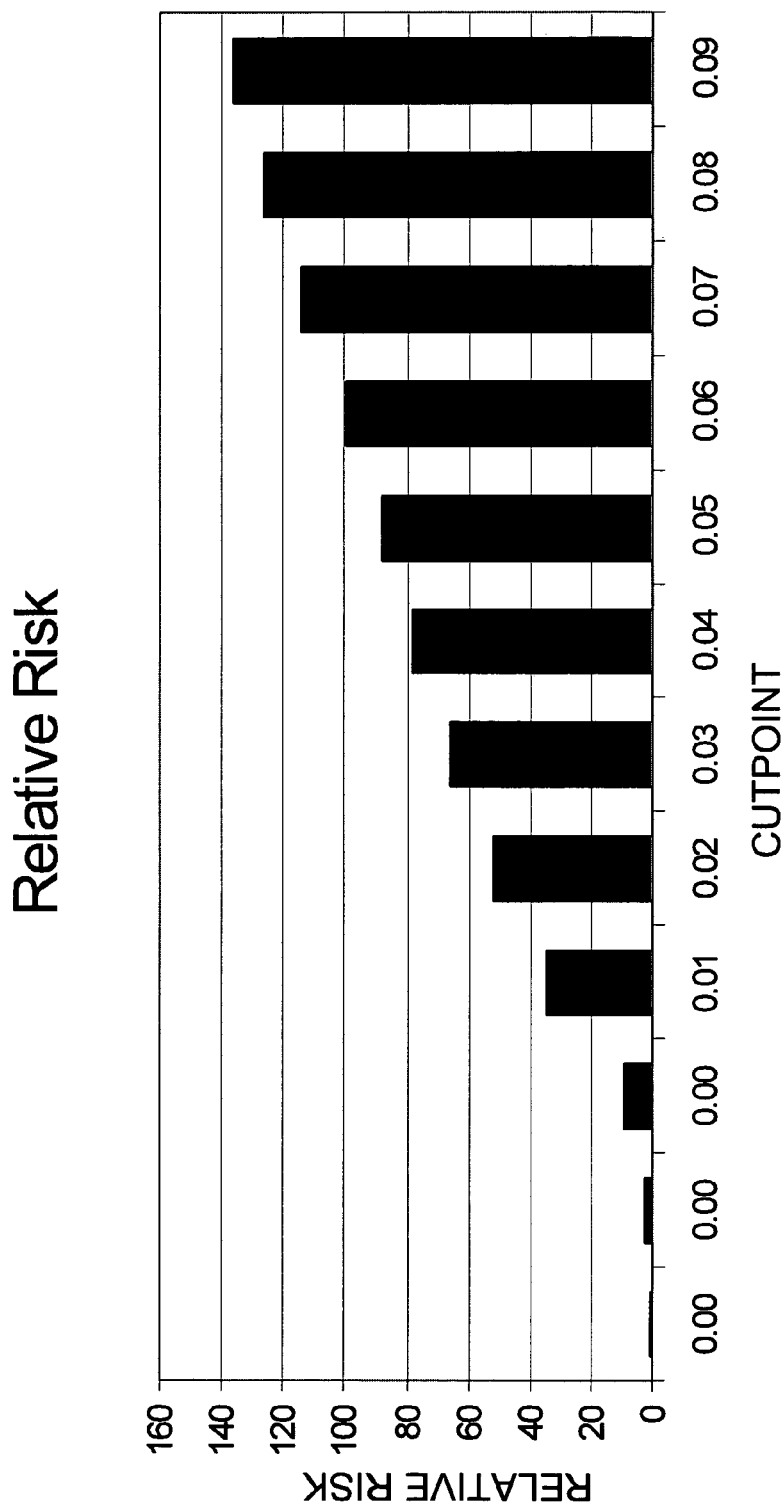
FIG. 8 is an exemplary graph of relative risk versus cut-point according to an illustrative embodiment of the invention.
Figure 9:
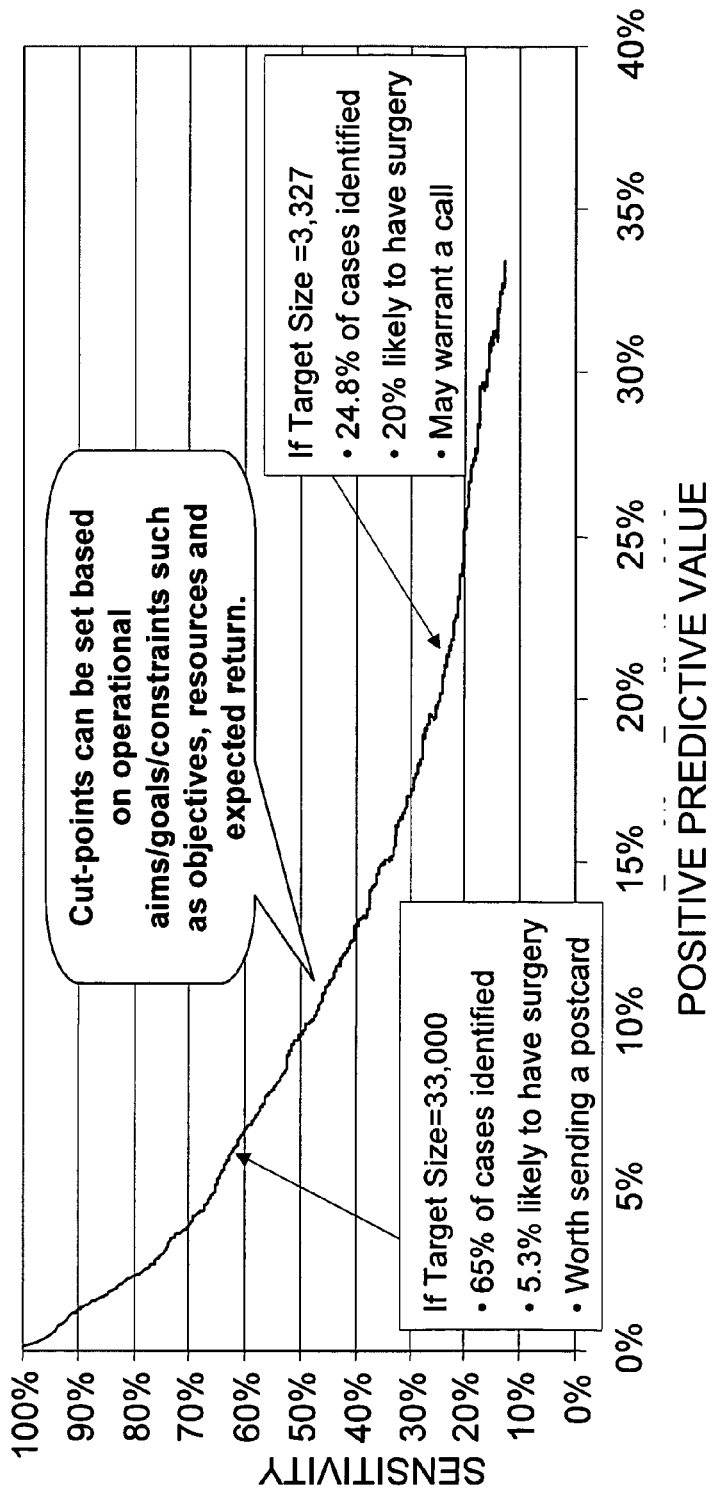
FIG. 9 is an exemplary graph of sensitivity versus positive predictive value for an exemplary back surgery predictive model according to an illustrative embodiment of the invention.

FIGS. 7-9 provide graphical illustrations of how, in one embodiment, the predictive model of the application 104 may be applied to predict surgical or diagnostic Risk—in this example, the risk of having back surgery. Alternatively, the predictive model of application 104 may be applied to predict the financial risk associated with back surgery. One purpose of the predictive model for back surgery is to identify beneficiaries at risk of back surgery using, for example, medical and pharmacy claims incurred within an actionable time period. Such a predictive model may identify members with back pain who can benefit from shared decision making enabled by the predictive model.

In one embodiment, the predictive model of application 104 for back surgery may be implemented according to an approach generally including 1) creating an analytic file of patient profile data 410 containing data for variables that may be related to back surgery and tend to occur more than 3 months before surgery (e.g., pharmacy claims for back pain medication, which may be likely to commence before the 3 months preceding surgery, as opposed to MRIs, which may be more likely to occur within the 3 months preceding surgery), and 2) running regression analyses to identify meaningful predictors of back surgery and develop a statistical model that tends to yield a meaningful predictive result when applied to patient profile data 410. For a particular data set, these predictors/risk factors may include certain patterns of physician visits coupled with pharmacy claims for medications associated with the treatment of back pain. In addition, various geographic and healthcare system factors 404 (such as healthcare system factor data, unwarranted geographic treatment pattern variations data, supply-sensitive factor data, and clinical care gaps) may be identified as significant in the development and validation of a predictive model for back surgery, such as the number of back surgeries per 1000 enrollees, the number of neurosurgeons or orthopedic surgeons per 100,000 residents, the number of physical medicine/rehabilitation facilities or practitioners per 100,000 residents, the number of unique providers seen, and visit frequency among PCPs and chiropractors. (See, e.g., FIGS. 5A and 5B.)

In one embodiment, a provider selects and/or identifies a set of predictors or independent variables that may be indicative of predicting a risk event and/or financial risk. The predictors may be selected manually based on provider experience and understanding of the medical conditions, medications, symptoms, and any other medical indicators of a future risk event. The predictors may then be programmed, submitted, and/or entered into a database such as database 106 to be accessed by the application 104. The predictors may be selected based on an analysis of existing patient data where common variables associated with a group or groups of patient that have experienced a particular risk event are identified, either by manual review or by an automated database 112, 114, 116, and 106 search and analysis. The application 104 may include a data mining process and/or subroutine to identify predictors associated with predicting a particular risk event. The data mining process may also be a separate application of the computer system 200 and/or another information system such as information system 110. Periodically, a panel of medical professionals may review and/or modify the set of predictors associated with a predicted risk event.

Once the predictors associated with a particular risk event such as back surgery are determined, the application 104 develops a predictive model based on patient data 402 extracted from one or more populations of patients and geographic/healthcare system data 404. A predictor may also be described as an independent variable or risk factor. In one exemplary embodiment, the application 104 employs one or more logistic regression models and/or stepwise logistic regression models to develop the predictive model for a back surgery risk event.

A logistic regression model may be preferable in relation to other regression models, such as a linear regression model, because the values of the dependent variable Y (e.g., the predicted risk event) are binary (0,1). In certain embodiments, the application 104 employs a logistic regression model to generate a logistic curve that relates an independent variable and/or predictor X to a rolling mean of the dependent variable Y as shown in the following formulas:

$$P = \exp(a+bX)/1+\exp(a+bX) \quad (1)$$

$$P = 1/1+\exp-(a+bX) \quad (2)$$

Where: P=the probability of a 1 (the proportion of 1s, the mean of Y)
exp=the base of the natural logarithm (approximately 2.718)
a=parameter, yields P when X=0
b (beta weight)=adjusts changes in P with changes in X
(note: b may be standardized or unstandardized)

Because the relationship or correlation between X and P is non-linear, the beta weight b does not have a linear interpretation as in ordinary linear regression modeling.

The application 104 preferably employs a maximum likelihood estimation (MLE) to determine the loss function for the above logistic curve. A likelihood may be considered a conditional probability of Y given X. Thus, in certain embodiments, the application 104 chooses parameters (a and b) of the logistic curve to estimate the best fitting curve that characterizes the relationship of the predictors X to the resulting risk event Y. In one embodiment, the parameters are chosen randomly. In another embodiment, the parameters are chosen based on a trial-and-error method. The estimates are called maximum likelihood estimates because the parameters are chosen to maximize the conditional probability of the relationship between X and Y.

In one embodiment, the application employs a numerical analysis to find the maximum likelihood estimates (MLEs). For example, the application 104 makes an initial estimate of the parameters. The application 104 computes the likelihood of the logistic curve based on the parameters. Then, the application 104 improves and/or adjusts the parameter estimates to a certain degree and re-calculates the likelihood of the logistic curve fitting the data. The application 104 continuously performs this likelihood estimation for a number of iterations and/or until the parameter changes are below a minimum amount. In certain embodiments, the maximum number of iterations is greater than or equal to about 50, about 100, about 200, about 500, and about 1000. In certain embodiments, the minimum amount of parameter change is less than about 0.1, about 0.01, and about 0.001.

By applying an MLE to determine the best fitting logistic curve of the relationship between each predictor X and risk event Y, the application 104 determines the beta weight b associated with each predictor and/or risk factor. Table 1 provides an exemplary table of the determined beta weights of predictors associated with predicting a lumbar back surgery risk event.

TABLE 1

Exemplary Predictors and beta Weights associated with Lumbar Back Surgery Risk Event

| Predictor Category (Element) | Predictor | Beta Weight |
|---|---|---|
| Demographic | age | 0.0321 |
| | male | 0.2030 |
| Diagnosis | Lumbar Back Pain | 1.1439 |
| | Unspecified Back Pain | 0.7158 |
| | Sciatica | 1.1300 |
| Procedure | Unspecified Back Myelography | 1.1555 |
| | Back Lumbar CAT Scan | 1.0010 |
| | Back Lumbar X-ray | 1.4451 |
| | Back Cervical X-ray | −0.3148 |
| | Unspecified Back X-ray | 0.3018 |
| | Disk Excision | 0.7762 |
| | Anesthetic Injections | 0.9280 |
| | Physical Therapy | 0.6247 |
| Pharmacy | Narcotic Analgesics | 0.3188 |
| | Anti-inflammatory Analgesics | 0.4372 |
| | Anti-depressents | 0.3296 |

TABLE 1-continued

Exemplary Predictors and beta Weights associated with Lumbar Back Surgery Risk Event

| Predictor Category (Element) | Predictor | Beta Weight |
|---|---|---|
| Specialist | Orthopedic Visit | 0.2692 |
| Geographic/Healthcare | HSA_primary | 0.0229 |
| Cost | Log_year1_cost | 0.4742 |

Table 1 includes predictors, predictor categories and/or elements, and beta weights associated with patient data 402 and geographic/healthcare system data 404 for a lumbar back surgery risk event. The application 104 may derive the beta weights of predictors associated with the demographics, diagnosis, procedures, pharmacy, and specialist categories based on the patient data 402. The application 104 may derive the beta weights of the predictors associated with geographic and cost categories from the geographic/healthcare system data 404 and/or other information sources.

In one embodiment, the geographic/healthcare system beta weight is derived from the rate of a medical condition and/or occurrence (or predictor) within a geographic and/or health care system area, such as a hospital service area (HSA), multiplied by the beta coefficient that associates the particular condition and/or predictor with the predicted risk event and/or financial risk. For example, the HSA primary predictor in Table 1 may be derived from the beta weight that correlates the number of physical medicine/rehabilitation facilities or practitioners with lumbar surgery risk events multiplied by the number of physical medicine/rehabilitation facilities or practitioners per 100,000 residents within the HSA of a particular patient.

Table 2 provides an exemplary listing of the beta coefficient and adjusted rate for the geographic/healthcare system predictor Medical Discharges (DRG) within, for example, a portion of the state of Massachusetts. In certain embodiments, adjusted rates are derived for health care regions and/or HSAs within any states, provinces, regions, territories, or countries, and other geographic and/or healthcare system segments to account for variations in the occurrence of particular risk events and/or financial risks. The variations may be unwarranted geographic treatment variations.

TABLE 2

Exemplary List of beta Weight Determination for Geographic/Healthcare System Variable Medical Discharges (DRG)

| Home Service Area | HSA number | Age/Sex adjusted rate | Rate*Beta coefficient |
|---|---|---|---|
| MA-Athol | 22002 | 275.8403472 | 0.090486667 |
| MA-Attleboro | 22003 | 255.7602388 | 0.083899589 |
| MA-Ayer | 22004 | 264.9613393 | 0.086917918 |
| MA-Beverly | 22005 | 224.8310859 | 0.073753589 |
| MA-Boston | 22006 | 282.136566 | 0.092552079 |
| MA-Brockton | 22007 | 298.7619729 | 0.098005878 |
| MA-Burlington | 22008 | 227.4512058 | 0.074613094 |
| MA-Cambridge | 22009 | 261.7359147 | 0.085859849 |
| MA-Clinton | 22010 | 300.1428059 | 0.098458846 |
| MA-Concord | 22011 | 215.9323691 | 0.070834454 |
| MA-Everett | 22013 | 345.3774771 | 0.113297628 |
| MA-Fall River | 22014 | 285.1100436 | 0.093527499 |
| MA-Falmouth | 22015 | 215.4991889 | 0.070692354 |
| US-United States | 99999 | 248.9081168 | |

Table 2 provides an exemplary list of the Medical Discharge (DRG) Rate per 1,000 Medicare Enrollees within a group of HSAs. Because the beta coefficient=0.00032804 for DRGs in this example, the beta weights are determined by multiplying the Adjusted Rate for a particular HSA with the beta coefficient for DRGs. The resulting beta weight for a particular HSA (shown in the fourth column) may then be summed with other beta weights to determine whether a particular patient has a susceptibility to a risk event and/or financial risk. Each HSA may be assigned an HSA number as shown in Table 2 to enable identification of a particular HSA. The application 104 may identify the HSA and/or other geographic/healthcare segment associated with a particular patient by determining the ZIP code of the patient's home address and/or the ZIP code of the location in which medical care is being administered. The Age/Sex Adjusted Rate (e.g., selected year period) indicates the number of medical discharges for that particular HSA over a period of time, e.g., the year 2001. The period of time employed may be at least about 3 months, 6 months, 12 months, and 24 months. In the circumstance where there are negative or suppressed rates associated with a particular HSA, an average value for the adjusted rate for a particular set of HSAs may be employed. For example, the average value for the adjusted rate for United States of America may be employed.

In certain embodiments, the application 104 uses the predictors and associated beta weights to predict risk events and/or financial risks. In another embodiment, the application 104 uses categories of predictors to predict risk events and/or financial risks. In one embodiment, the application 104 uses the adjusted geographic/healthcare beta weights of Table 2 for predicting risk events and/or financial risks. In another embodiment, the application 104 uses non-adjusted geographic/healthcare beta weights and/or beta coefficients for predicting risk events and/or financial risks.

In one embodiment, the application 104 determines the odds that a risk event and/or financial risk occurs according to the following formula:

$$\text{Odds} = P/1 - P \quad (3)$$

where: P=the probability that a risk event occurs
1−P=the probability that a risk event does not occur In logistic regression, the dependent variable Y (e.g., risk event) can be express as a logit which is dependent on the Odds of the dependent variable. Thus, the application 104 may express the logistic regression by the following formula:

$$\text{Log(Odds)} = \text{logit}(P) = \ln(P/1 - P) \quad (4)$$

Therefore, because the logit is a log of the Odds and the Odds are a function of P (P=1), the logistic regression may be expressed as a linear expression and/or curve by the following formula:

$$\text{Log(Odds)} = \text{Logit}(P) = a + bX \quad (5)$$

Thus, while the log Odds are linearly related to the predictors X, the probability P of a risk event is non-linearly related to the predictors X. Because the Log (Odds)=a+bX, Equation (2) can be expressed as:

$$RS(\text{risk score}) = P = 1/1 + \exp - (\text{Log(Odds)}) \quad (6)$$

Assuming that the predictor X may be expressed using a binary 1 ("predictor flag") when the predictor is present in a patient profile, the Log (Odds) including multiple predictors may be expressed as:

$$\text{Log(Odds)} = \text{sum of (predictor flag*beta weights)} \quad (7)$$

Accordingly, a risk score RS and/or probability P of Equation (6) may be employed to determine a risk score associated with a portion of the patients in a population to determine which patients are most susceptible to a particular risk event. Using Equations (6) and (7), the application 104, in certain embodiments, calculates a risk score based on the predictors identified in a patient profile 410. For example, if a patient profile 410 for patient A includes predictor and/or condition flags associated with the predictors age, back lumbar X-ray, and MA primary care, Equation (7) is calculated as:

Log(Odds)=0.321+1.4451+0.0229=1.789

Therefore, the risk score RS for patient A to incur a lumbar back surgery event is calculated as:

RS=1/1+exp−(1.789)=0.857 or as P=85.7%

The risk score RS, in this instance, is the probability P that the risk event, e.g., lumbar back surgery, occurs due to the three predictors and/or risk factors identified in Patient A profile 410. Patient B may have three other predictors associated with the lumbar back surgery risk event and have a RS=0.812. Patient C may have one predictor associated with the lumbar back surgery risk event and have a RS=0.321. In one embodiment, the application 104 determines the RS for each patient within a group of patients. The application 104 then determines a portion of patients with a range of susceptibility to the lumbar back surgery risk event based on the range of risk scores of the patients. The most susceptible patients have the highest risk scores and the least susceptible patients have the lowest risk scores.

In certain embodiments, the application 104 may express financial risk associated with a particular risk event as follows:

$$PC(\text{predicted cost})=\exp(\text{Log(Odds)}) \quad (8)$$

An associated financial risk score (FRS) may also be express as follows:

$$FRS(\text{financial risk score})=PC/C \quad (9)$$

where: C is a constant such as 20000.
For example, the PC and FRS for patient A above are calculated as:

PC=exp(1.789)=5.984

FRS=5.984/20000=0.00299

With regard to the risk score, patient A may be ranked among a group of patients to determine which portion of patients posses a certain range of financial risk associated with lumbar back surgery. In other embodiments, financial risk may be expressed in the form of a probability and/or risk score according to the formula (6). Other values and/or risk totals may be employed to rank and/or identify one or more patients within a patient population with a range of susceptibility to a risk event and/or financial risk. The risk totals may include, without limitation, standardized and/or normalized beta weights, unstandardized and/or unnormalized beta weights, probabilities, propensity scores, financial costs, and like weight scores. The risk total score range may be adjusted and/or normalized to a particular range such as 0-1, 0-10, 0-50, 0-100, 0-1000 and like numerical ranges. The score may be expressed as a percentage, fraction, chart, scale, bar graph, plot, and any other image that depicts the predicted risk event and/or financial risk.

In one embodiment, the application 104 employs one or more chi-square tests such as a model chi-square and/or likelihood ratio test to statistically test whether a particular predictor reduces the badness-of-fit measure or increases the goodness-of-fit measure. If the chi-square is significant, a predictor is considered to be a significant predictor in the model which is analogous to the beta weight in a simultaneous logistic regression. The chi-square test may include a stepwise and/or sequential logistic regression. In one embodiment, the likelihood ratio, also known as the likelihood ratio chi-square has a probability value of greater than about 0.05 for a well-fitting model.

Certain patients may be excluded from intervention plans because they are less likely to benefit from shared decision making for preference sensitive decisions (PSD). This could either be due to the presence of a condition that takes priority over the PSD or a clinical reason and/or designation indicating that the risk event and/or surgical decision is not preference sensitive. Accordingly, the application 104 may exclude certain patients from the prediction model analysis based on designated exclusion facts. The following exemplary list of patient profile 410 facts may be used to exclude certain patients and/or healthcare system members from PSD targeting for lumbar back surgery.

Spine Trauma
Osteomyelitis
Lumbar Back Surgery in previous 12 months
AIDS
Any Cancer Certain facts may be specific to certain models. For example, the AIDS and cancer exclusions, in one instance, may be specific to the lumbar back model.

In certain embodiments, the application 104 may determine and output certain performance benchmarks. Table 2 lists some performance metrics for a predictive model such as the lumbar back predictive model. The measures may be based on validation reports derived from empirical data regarding actual outcomes from one or more interested parties. Each measure may be based on patients that are identified as being in the top 10 risk groups. There may be a significant amount of variation in model performance between different interested parties and/or payors which may be taken into account when predicting risk events and/or financial risk, identifying intervention opportunities, and defining target lists of patients for intervention.

TABLE 3

Exemplary Predict Model Performance Metrics

| Interested Party | Percent of Population | Relative Risk | Sensitivity | PPV |
|---|---|---|---|---|
| Payor A (top 10) | 4% | 8.04 | 25% | 6.9% |
| Payor B (top 10) | 3% | 9.58 | 20% | 4.8% |
| Payor C (top 10) | 10% | 4.59 | 34% | 4.2% |
| Payor (top 10) | 0% | 4.96 | 2% | 4.7% |

In the exemplary Table 3, the relative risk is the ratio of surgery rates and/or predicted risk events for identified patients to the general population. A relative risk greater than 1 may indicate that the identified group has a higher surgery and/or risk event rate. Larger values may indicate a greater difference. Sensitivity indicates the proportion of all surgeries and/or risk event that were captured by the group. The Positive Predictive Value (PPV) is the percent of identified patients that incurred a risk event.

While the $R^2$ value may be appropriate for certain regression models such as linear regression models, the $R^2$ value may not provide a sufficiently accurate measure when the application 104 employs a logistic regression model. However, the $R^2$ value may be utilized with a logistic regression if desired with an understanding of its limitations. As an alternative to the $R^2$ value, the application 104 may employ, without limitation, the Cox and Snell's R-square, the Nagelkerke R-square, the R1-square, and R1a-square, and like values.

In one embodiment, the application 104 employs a linear regression model to predict risk outcomes such as risk events and/or financial risk. The application 104 may employ other model including, without limitation, the log-linear, logit, and/or probit regression models to predict risk events and/or financial risk. A predictive model may include multiple regression models. In one embodiment, a separate regression model is applied to each variable.

In one illustrative embodiment, the predictive model component 412 of application 104 also includes stratifications wherein regression models produce continuous risk scores. Stratification permits the size of the targeted population to be set based on various factors, such as resources or objectives.

FIG. 7 is an exemplary receiver-operating characteristic (ROC) curve of sensitivity versus specificity according to an illustrative embodiment of the invention and provides an illustration of potential ROC Curve metrics for the operating characteristics of a predictive model of the application 104 for back surgery. It illustrates an association of predicted probabilities and observed responses (in this example, 85.7% concordant; 1.9% discordant; 12.4% tied; c=0.919).

FIG. 8 is an exemplary graph of relative risk versus cut-point according to an illustrative embodiment of the invention and provides an illustration of further potential metrics for the operating characteristics of a predictive model of the application 104 for back surgery. It illustrates relative risk as a function of different cut-points that may be selected.

FIG. 9 is an exemplary graph of sensitivity versus positive predictive value for an exemplary back surgery predictive model according to an illustrative embodiment of the invention and illustrates examples of the potential flexibility and tradeoffs available with a predictive model of the application 104 for back surgery by comparing sensitivity against positive predictive value. As indicated in FIG. 8, different cut-points can be selected for different operational aims, goals or constraints (such as objectives, resources, and expected return).

Figure 10:
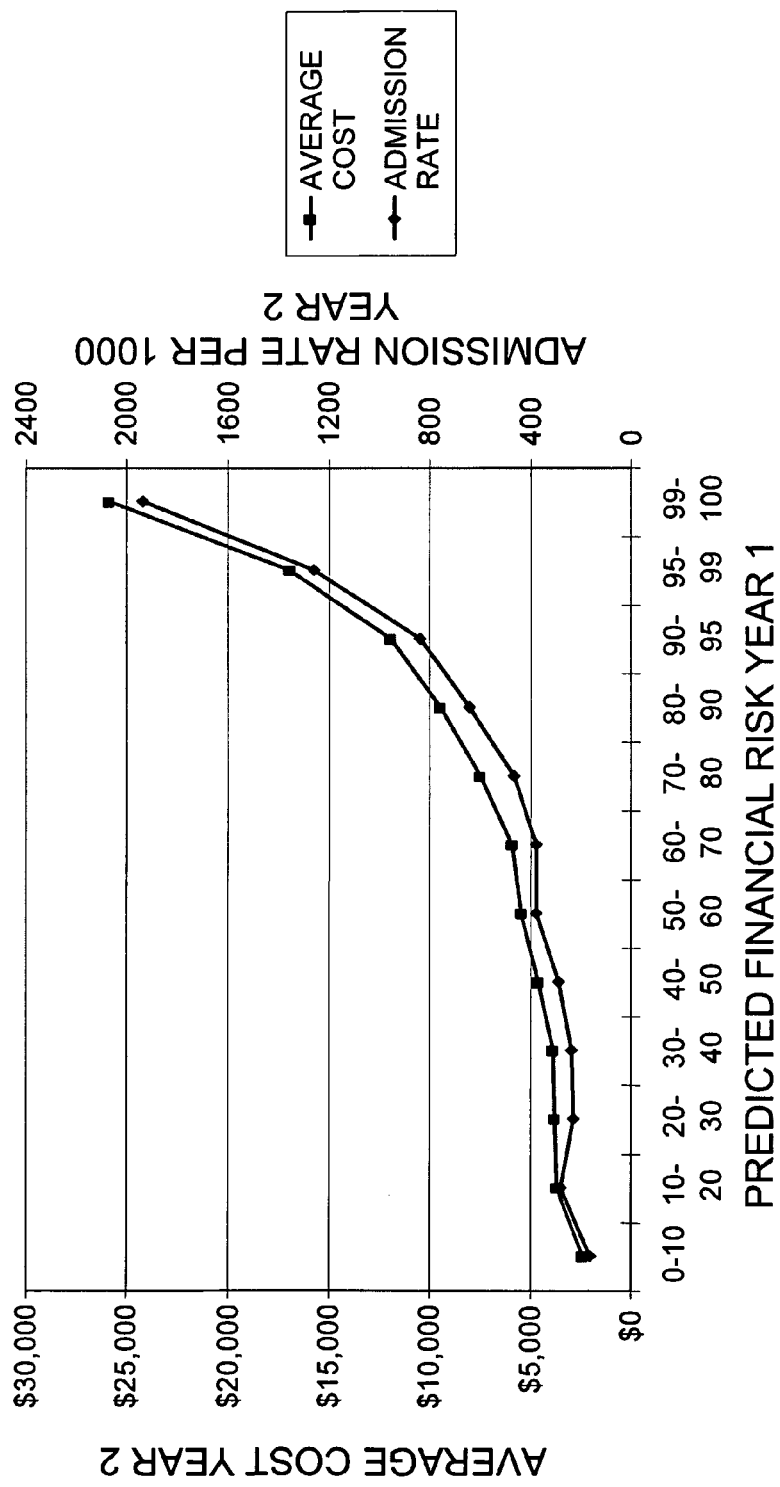
FIG. 10 is an exemplary graph of average cost in Year 2 versus predicted average cost in Year 1 according to an illustrative embodiment of the invention.

FIG. 10 is an exemplary graph of average cost in Year 2 versus predicted average cost based on Year 1 claims according to an illustrative embodiment of the invention and provides a graphical illustration of the predicted cost as modeled by an exemplary financial risk model of the application 104. In one embodiment, an R-square value of 0.30 is reflective of standard model parameters. In this exemplary illustration, the estimates are based on a total population of 2 million members. However, other population sizes may be employed.

As evidenced by the foregoing discussion and illustrations, the predictive modeling analytic systems and methods of the invention are useful in a wide range of applications. While this invention has been particularly shown and described with reference to preferred embodiments thereof, it will be understood by those skilled in the art that various changes in form and details may be made therein without departing from the scope of the invention encompassed by the appended claims. In certain embodiments, the term 'event risk' may mean and/or refer to a "risk event," and/or refer to the risk of the occurrence of a risk event.

It will be apparent to those of ordinary skill in the art that methods involved in the present invention may be embodied in a computer program product that includes a computer usable and/or readable medium. For example, such a computer usable medium may consist of a read only memory device, such as a CD ROM disk or conventional ROM devices, or a random access memory, such as a hard drive device or a computer diskette, or flash memory device having a computer readable program code stored thereon.

What is claimed is:

1. A system for predicting healthcare financial risk comprising:
   a computer;
   a computer readable medium, operatively coupled to the computer, the computer readable medium storing program codes causing the computer to perform functions comprising:
   accessing patient data associated with one or more patients,
   accessing geographic and healthcare system data, the geographic and
   healthcare system data including unwarranted treatment pattern variation data, wherein the unwarranted treatment pattern variation data includes any variation in treatment across different geographic regions or healthcare systems that is based on healthcare provider behavior which is not in accordance with established evidenced-based clinical guidelines and not caused by patient preferences or physical characteristics,
   defining a plurality of unwarranted treatment pattern variation adjustment values, each unwarranted treatment pattern variation adjustment value being associated with a particular geographic region or healthcare system,
   modifying a portion of the patient data based on at least one of the plurality of unwarranted treatment pattern variation adjustment values, and
   applying a predictive model to the modified patient data to generate patient profile data and to identify a portion of the patients associated with a range of predicted financial risk.

2. The system of claim 1 comprising categorizing one or more patients into one or more clinical segments and applying the predictive model to each clinical segment.

3. The system of claim 2, wherein the segments are based on at least one of preference sensitive conditions, chronic diseases, and large medical cases not associated with chronic disease.

4. The system of claim 1, comprising generating one or more facts based on the patient data, geographic data, or healthcare system data.

5. The system of claim 1 comprising reporting the portion of the patients associated with a range of predicted financial risk to at least one of a healthcare provider, a healthcare insurer, and a payor.

6. The system of claim 1 comprising generating a suggested intervention plan for one or more patients based on a range of predicted financial risk.

7. The system of claim 1, wherein the patient data includes patient claims data and patient non-claims data.

8. The system of claim 7, wherein patient claims data includes at least one of medical claims data and pharmacy claims data.

9. The system of claim 7, wherein patient non-claims data includes at least one of referral data, functional status data, laboratory values, patient risk factors, demographics, disease burden, and disease complications.

10. The system of claim 1, wherein geographic data includes geographic practice pattern variables.

11. The system of claim 1, comprising filtering the patient data, geographic data, and healthcare system data into clean data, wherein filtering includes:
    importing patient data files,
    mapping patient data into standard formats,
    processing adjustments and duplicates,
    checking patient data parameters against internal and external normal parameters,
    identifying and correcting data errors, and creating a table to link patient data to unique patient identifiers.

12. The system of claim 1, wherein applying the predictive model includes:
separating patient data into a first and second data set,
evaluating regressively one or more risk factors in the first data set to determine weights associated with significant risk factors, and
applying the weights for each significant risk factor to the second data set to validate the predictive model performance.

13. The system of claim 12 comprising applying at least one of a linear regression model, a non-linear regression model, a logistic regression model, a Bayesian network model, a Markov model, and a propensity score to evaluate the risk factors.

14. The system of claim 12 comprising adding the weights associated with the risk factors associated with one or more patients to generate risk totals associated with the one or more patients.

15. The system of claim 14 comprising identifying a portion of the patients associated with a level of predicted financial risk by identifying a portion of the one or more patients with the highest risk totals.

16. The system of claim 12, wherein the weight includes a beta weight.

17. The system of claim 16 comprising deriving a risk score based at least in part on the beta weight.

18. The system of claim 17, wherein the risk score includes a value in the range of 0 to 1.

19. The system of claim 12, wherein validating includes applying a goodness-of-fit measure.

20. The system of claim 1, wherein applying the predictive model includes:
separating patient data into a first and second data set,
evaluating regressively one or more risk factors in the first data set to determine weights associated with significant risk factors,
evaluating regressively one or more risk factors in the second data set to determine weights associated with significant risk factors, and
comparing the weights of risk factors of the first data set with the weights of the risk factors of the second data set.

21. The system of claim 1 comprising refining and validating the risk predictive model by comparing patient profile data of a first portion of patients with patient profile data of a second portion of patients.

22. The system of claim 21, wherein the refining and validating include:
dividing the patient profile into a model development data set and a model validation data set,
applying weights to the model development data set to profile the model validation set.

23. The system of claim 22, wherein the data includes one or more variables.

24. The system of claim 23, wherein a variable includes one of age, gender, log transformed cost for the first period, number of specialist visits, primary care capacity, and a condition flag.

25. The system of claim 24, wherein a condition flag is associated with patient clinical condition.

26. The system of claim 22, wherein the model development data includes patient claims data associated with a first period of time and the model validation data is associated with a second.

27. The system of claim 1, wherein the portion of the patients associated with a range of predicted financial risk includes a selected percentage of the patients that represent the highest financial risk.

28. The system of claim 1, wherein the portion of the patients associated with a range of predicted financial risk includes a selected percentage of the patients that represent the lowest financial risk.

29. The system of claim 1, wherein the portion of patients associated with a range of predicted financial risk includes patients representing a selected spectrum of financial risk.

30. A non transitory computer readable medium having computer readable program codes embodied therein for predicting healthcare financial risk, the computer readable medium storing program codes causing the computer to perform functions comprising:
accessing patient data associated with one or more patients,
accessing geographic and healthcare system data, the geographic and healthcare system data including unwarranted treatment pattern variation data, wherein the unwarranted treatment pattern variation data includes any variation in treatment across different geographic regions or healthcare systems that is based on healthcare provider behavior which is not in accordance with established evidenced-based clinical guidelines and not caused by patient preferences or physical characteristics,
defining a plurality of unwarranted treatment pattern variation adjustment values, each unwarranted treatment pattern variation adjustment value being associated with a particular geographic region or healthcare system,
modifying a portion of the patient data based on at least one of the plurality of unwarranted treatment pattern variation adjustment values, and
applying a predictive model to the modified patient data to generate patient profile data and to identify a portion of the patients associated with a range of predicted financial risk.

* * * * *